(12) United States Patent
Graziosi

(10) Patent No.: US 6,277,567 B1
(45) Date of Patent: *Aug. 21, 2001

(54) METHODS FOR THE CONSTRUCTION OF GENEALOGICAL TREES USING Y CHROMOSOME POLYMORPHISMS

(75) Inventor: Giorgio Graziosi, Trieste (IT)

(73) Assignee: Fitolink Corporation, Mount Laurel, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/025,336

(22) Filed: Feb. 18, 1998

Related U.S. Application Data

(60) Provisional application No. 60/038,050, filed on Feb. 18, 1997.

(51) Int. Cl.[7] ............................... C12Q 1/68; C12P 19/34
(52) U.S. Cl. ................................. 435/6; 435/91.2
(58) Field of Search ........................ 435/6, 91.2

(56) References Cited

PUBLICATIONS

Santos et al., Human Genetics, vol. 97, pp. 309–313, 1996.*
Matias et al., Human Molecular Genetics, vol., 3, pp. 115–123, 1995.*
Amanda B. Spurdle, et al., "The Y Alu polymorphism in Southern African Populations and Its Relationship to Other Y–specific Polymorphisms", Am.J.Hum.Genet. 54;319–330, 1994.
P. Malaspina, et al., "The human Y chromosome shows a low level of DNA polymorphism", AM.J.Hum.Genet. (1990), 54:297–305, Printed in Great Britian.
Michael F. Hammer al., Y Chromosomal DNA Variation and the Peopling of Japan, Am.J.Hum.Genet. 56:951–962, 1995.
Michael F. Hammer et al, "A recent common ancestry for human Y chromosomes", Nature vol. 378, Nov. 23 1995, pp. 376–378.
D. B. Goldstein, et al., "Genetic absolute dating based on microsatellites and the orgin of modern humans", Proc.Natl.Acad. Sci. USA, vol. 92, pp. 6723–6727, Jul. 1995 Evolution.
Fabricio Rodrigues Santos, et al., "PCR haplotypes for the human Y chromoson based on alphoid satellite DNA variants and heteroduplex analysis", Gene. 165 (1995) 191–198.
John Maynard Smith, "Human Evolution, The Y of Human relationships", Nature vol. 344 Apr. 12 1990, pp. 591–592.

* cited by examiner

*Primary Examiner*—Lisa B. Arthur
*Assistant Examiner*—Jehanne Souaya
(74) *Attorney, Agent, or Firm*—Dann, Dorfman, Herrell and Skillman

(57) ABSTRACT

Methods are disclosed for the determination of degree of relatedness between individuals having the same or different surnames, based on comparisons of specific Y chromosome polymorphisms.

2 Claims, 8 Drawing Sheets

METHODS FOR THE CONSTRUCTION OF GENEALOGICAL TREES USING Y CHROMOSOME POLYMORPHISMS

This application claims priority under 35 U.S.C. §119(e) to U.S. Ser. No. 60/038,050, filed Feb. 18, 1997.

FIELD OF THE INVENTION

This invention relates to the fields of molecular biology and evolution. Specifically, the invention provides materials and methods for assessing the degree of relatedness between individuals with the same surname.

BACKGROUND OF THE INVENTION

Several publications are referenced in this application by author name, year and journal of publication in parentheses in order to more fully describe the state of the art to which this invention pertains. The disclosure of each of these publications is incorporated by reference herein.

Molecular biology has played a pivotal role in the analysis of human diversity. Prior to the development of this branch of science, historians, archaeologists and anthropologists analyzed artifacts and recorded history to study events in the remote past. In the last few years new techniques have been generated allowing an inside view of human history and development by analysis of the variations contained in human DNA. Studies conducted on mitochondrial DNA (Di Rienzo and Wilson, (1991) Proc. Natl. Acad. Sci. 88:1597–1601) provided relevant data relating to the origin of modern man. The data from this study suggest that human beings descended from one women who lived in Africa 1–2,000 centuries ago (Ayala and Escalante, (1996) Mol. Phylogenet. Evol. 5:188–201)

The counterpart of the maternally inherited mitochondrial DNA is represented by the Y chromosome which is transmitted along the male line from fathers to sons. The study of the variations (mutations) of the human Y chromosome facilitates the investigation of the history of this chromosome and related members of a given male line. Research is currently being conducted regarding the origin and diversity of man by comparing the Y chromosome of different populations. These studies are being conducted on a world-wide level (Spurdle and Jenkins, (1992) Curr. Opin. Genet. Dev. 2:487–491; Santos et al., (1996) Hum. Gen. 97:309–313).

Rather than the developmental history of whole populations, individuals are often more interested in recent history and ultimately in knowing who their kin are beyond the restricted circle of their close relatives. In western culture, a simple way of identifying families and kin is the attribution of a surname. However, people with the same surname are not always related.

The present invention provides compositions and methods for performing genetic analyses which compare surnames and Y chromosome polymorphisms. The feasibility of identifying close relatives, distant relatives and those unrelated in a male line is demonstrated herein. Additionally, methods for constructing a "Genealogical Tree" of close and distant kin are disclosed.

SUMMARY OF THE INVENTION

The present invention provides methods and materials for use in determining degree of relatedness between male individuals based on surnames and Y chromosome haplotypes.

In one embodiment of the invention, DNA is isolated from biological samples obtained from male individuals with the same surname and the degree of relatedness between the individuals is determined based on the presence and number of polymorphisms identified on the Y chromosome. Similar assays may be performed on individuals with different surnames who suspect they may be related to one another. Thus, the present invention provides methods for assessing familial relationships and human diversity.

DETAILED DESCRIPTION OF THE INVENTION

Figure 1:
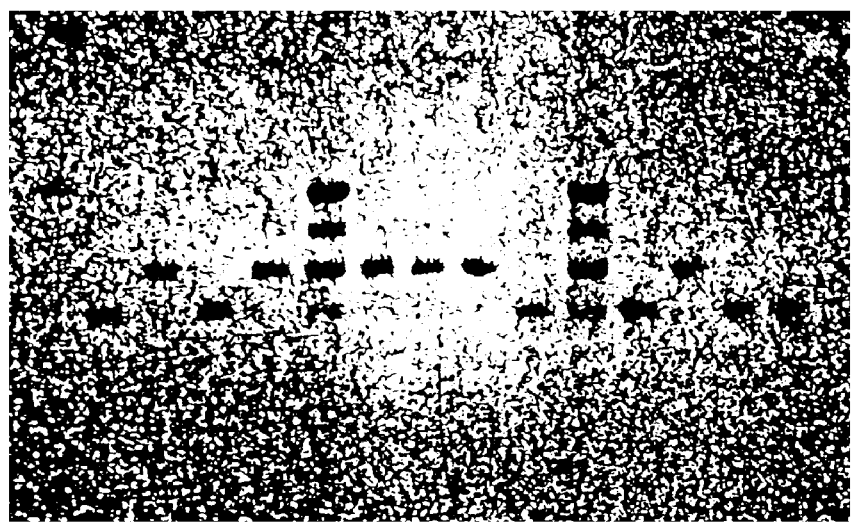
FIG. 1 depicts a gel showing the results of electrophoresis of amplified DYS393 fragments isolated from members of the Bassi family.

In the majority of western countries, new-born babies inherit their surname from their fathers. Males also inherit the Y chromosome from their fathers. A significant portion of the Y chromosome does not undergo meiotic recombination during spermatozoa maturation and therefore the DNA sequence of this chromosome is inherited as a single packet.

In the last few years a number of polymorphic loci of the Y chromosome have been identified (Roewer et al., 1992). This allows for the characterization of a very large number of different Y chromosomes. In accordance with the present invention, methods are provided which facilitate the identification of different Y chromosomes by their haplotypes and then correlate the association of a specific haplotype to a specific surname or group of surnames.

Haplotype is defined in Stedman's Medical Dictionary as follows: "The genetic constitution of an individual with respect to one member of a pair of allelic genes; individuals are of the same haplotype (but of different genotypes) if alike with respect to one allele of a pair but different with respect to the other allele of a pair; a particular combination of alleles in a defined region of a chromosome". Haplotype was originally used to describe combinations of MHC alleles. The term is now often used to describe particular combinations of polymorphic loci. Haplotypes can be analysed by gene amplification (PCR), Multiple Variant Repeats or by Southern blot. These last three procedures are set forth in *Current Protocols of Molecular Biology*, Ausubel et al. eds, J W Wiley and Sons, 1995, the disclosure of which is incorporated herein by reference.

The human Y chromosome has two small regions (Pseudo Autosomic Region, PAR1 and PAR2) which are homologous to small portions of the X chromosome. The two PAR regions undergo genetic recombination while the rest of the chromosome is transmitted from one generation to the other as a non-recombinant single block. Therefore, specific haplotypes represent a constant characteristic of a given Y chromosome, mutation being the only source of variation. Mutation of Y chromosome minisatellites is a relatively rare event and, normally, should affect only one locus at a time. One haplotype is therefore derived from an other haplotype by mutation in a single locus over time. Different Y chromosomes will accumulate different mutations and will progressively diverge. By analyzing the reverse of this process, it is possible to reconstruct the evolutionary history of a haplotype inside a given population.

Different Y chromosome haplotypes can be connected one to the other joining the most similar one to form a treelike figure used to graphically represent a hierarchy, i.e., a dendrogram. The process can be rather complex and it is convenient to add haplotypes one by one. At any addition of a new haplotype, the entire dendrogram must be revised and eventually completely reshaped to respond to the rule of "parsimony". A dendrogram will fulfil this rule when the total sum of mutations among the connected haplotypes is minimal.

Two haplotypes are compared gene-by-gene in the following way:

1) if all the loci show identical alleles, then the two haplotypes are considered identical;
2) if only one locus shows a different allele, then one mutation is scored, independently from the type of the variation (allele);
3) if two loci show a different allele, two mutations are scored irrespective from the variation; and if n loci show different alleles, then n mutations are scored irrespective from the type of variation. These principals are illustrated by the following example.

| LOCUS   | haplotype1 | haplotype2 | haplotype3 | haplotype4 |
|---------|------------|------------|------------|------------|
| DYS19   | 1          | 1          | 1          | 1          |
| DYS388  | 1          | 2          | 1          | 2          |
| DYS389A | 3          | 3          | 3          | 3          |
| DYS389B | 5          | 5          | 5          | 5          |
| DYS390  | 5          | 5          | 1          | 1          |
| DYS391  | 3          | 3          | 3          | 3          |
| DYS392  | 2          | 2          | 2          | 2          |
| DYS393  | 2          | 2          | 2          | 2          |

Comparing haplotypes 1, 2, 3, and 4 above, it can be seen that the following haplotypes show one mutation (one different locus):

1–2 (different at the DYS388 locus)
1–3 (different at the DYS390 locus)
2–4 (different at the DYS390 locus)
3–4 (different at the DYS388 locus)
The following haplotypes differ for two mutations:
1–4 (different at the DYS388 and DYS390 loci)
2–3 (different at the DYS388 and DYS390 loci)

The four haplotypes shown can be connected one to the other to form a dendrogram but this process may have more than one solution. In this simple case the possible minimum spanning combinations are two:

2--------1--------3--------4   or
total number of mutations = 3
4--------2--------1--------3
total number of mutations = 3

Thus, the two dendrograms are equivalent because both connect haplotypes differing only for one mutation. Haplotype 4 cannot be connected directly to haplotype 1 because this connection would increase the total number of mutations required to justify the dendrogram. Finally, direct connection between two haplotypes differing for two or more loci is allowed when the intermediate haplotype was not found.

A priori one would not expect a stringent correspondence between Y chromosome haplotypes and surnames for the reasons set forth below.

A) Polyphyletic Origin of Surnames

People with the same surname are not necessarily related. In fact the same surname may have originated independently at different times and in different places and its holders may not be biologically connected at all. A typical example of such a case is provided by surnames which derive from specific professions: not all the Smiths, Schmidt or Fabbro belong to the same family since each village had their own smith and, consequently, their own Smith family with its corresponding specific Y chromosome haplotypes.

B) Non-paternity

When the biological father is different from the legal father, a discrepancy between the inheritance of the surname and the inheritance of the Y chromosome is introduced. Typical cases are adoptions, children receiving the surname from the mother and children conceived outside the marriage.

C) Changes of Surnames

The correspondence between a surname and a haplotype can be disrupted by the change of the surname or erroneous transcription of the surname.

D) Mutation

Polymorphic sequences known as mini- or microsatellites have relatively high frequencies of mutation. A mutation would introduce a variant Y chromosome haplotype within a family.

All of the factors listed above have been acting for centuries, beginning from the origination of a given surname. Today, the correspondence between a surname and a given Y haplotype may be considerably disrupted. Nevertheless there are factors counteracting this disruption, e.g., high fecundity of certain families, and geographical isolation. Some clustering of haplotypes and surnames is expected, but statistics on this subject are not available. The percentage of correspondence between surnames and Y chromosome haplotypes has been evaluated in accordance with the present invention in the population studies described in Examples I–III.

Four levels of sampling were utilized in the present application: town (Trieste, 220,000 inhabitants), province (Friuli, 520,000 inhabitants), nation (Italy, 57 millions inhabitants) and world wide level. The haplotypes identified in the samples isolated from Trieste and Friuli are shown in Table III.

The following examples are provided to describe the invention in further detail. These examples are intended merely to illustrate and not to limit the invention.

EXAMPLE I

Town Level Sampling

Methods

More than 700 random blood samples were collected in the town of Trieste. The samples were obtained during a fixed period of time from blood donors willing to contribute to the research. All donors provided their surname and were interviewed on the name and the place of birth of their paternal grandfather. At the end of sample collection, only the surnames which appeared in duplicate or more (48 surnames) were taken in account and the corresponding blood samples were subjected to molecular analysis of 8 polymorphic Y chromosome loci. The 106 donors with surname in duplicate or more were interviewed again to establish possible kinship. All donors declaring relatedness up to the degree of second cousin were considered as relatives. All other donors were initially considered unrelated.

DNA Extraction

DNA was extracted from blood samples by standard phenol-chloroform purification.

Finger nail tips were washed for one hour in 1X SSC and Tween 0.5%, lysed for 12 hours at 56° C. in 250 µl Na acetate 0.2M, EDTA 10 mM, 35 mM DTT, 150 µg proteinase K. DNA was treated with Diatomaceous Earth in guanidinium hydrochloride 5M and finally eluted with 30 µl of double distilled water at 68° C.

PCR

A total of 106 Trieste blood samples with 48 surnames and 106 Friuli samples with 9 surnames were analysed by gene amplification (PCR). The following polymorphic loci of the human Y chromosome were amplified: DYS19, DYS388, DYS389A, DYS389B, DYS390, DYS391, DYS392, DYS393.

The PCR parameters adopted were those reported by Roewer et al. (1996) with modifications as reported below:

DYS19—1 long cycle denaturation (4 minutes at 94° C.); 26 cycles of denaturation (30 minutes at 94° C.); annealing (30 minutes at 51° C.); and synthesis (90 minutes at 72° C.).

DYS388—1 long cycle denaturation (4 minutes at 94° C.); 28 cycles of denaturation (30 minutes at 94° C.); annealing (30 minutes at 55° C.); and synthesis (60 minutes at 72° C.).

DYS389—1 long cycle denaturation (4 minutes at 94° C.); 28 cycles of denaturation (30 minutes at 94° C.); annealing (30 minutes at 55° C.); and synthesis (60 minutes at 72° C.).

DYS390—1 long cycle denaturation (2 minutes at 94° C.); 5 cycles of denaturation (15 minutes at 94° C.); annealing (15 minutes at 58° C.); and synthesis (20 minutes at 72° C.); 30 cycles denaturation (15 minutes at 94° C.); annealing (15 at 54° C.); and synthesis (20 minutes at 72° C.).

DYS391—1 long cycle denaturation (2 minutes at 96° C.); 2 cycles denaturation (30 minutes at 96° C.); annealing (30 minutes at 640C); synthesis (30 minutes at 72° C.); 2 cycles denaturation (30 minutes at 96° C.); annealing (30 minutes at 60° C.), synthesis (30 minutes at 72° C.); 28 cycles denaturation (30 minutes at 96° C.); annealing (30 minutes at 58° C.); and synthesis (30 minutes at 72° C.).

DYS392—1 long cycle denaturation (2 minutes at 94° C.); 5 cycles of denaturation (15 minutes at 94° C.); annealing (15 minutes at 58° C.); and synthesis (20 minutes at 72° C.); 30 cycles denaturation (15 minutes at 94° C.); annealing (15 at 54° C.); and synthesis (20 minutes at 72° C.).

DSY393—1 long cycle denaturation (2 minutes at 94° C.); 30 cycles of denaturation (15 minutes at 940C); annealing (15 minutes at 58° C.); and synthesis (20 minutes at 72° C.).

The samples of Trieste were analysed also for the two loci of YCA2 as reported (Mathias et al. (1994) in Hum. Mol. Genet. 3:115–123) with modifications as reported below:

YCA2—1 long cycle denaturation (2 minutes at 94° C.); 30 cycles of denaturation (60 minutes at 94° C.); annealing (60 minutes at 50° C.); and synthesis (90 minutes at 72° C.).

The amplified fragments were separated by electrophoresis on 6–9% acrylamide gels and the gels subsequently silver stained. An example of the PCR analysis on polymorphisms for DYS393 is provided in FIG. 1 based on Y chromosome analysis in a sample from the Bassi family.

RESULTS

The results of molecular analysis of the samples collected in Trieste are set forth in Table I. The alleles were designated by numbers assigning 1 to the smallest allele of each locus. The last column of Table I reports the comprehensive haplotype of each sample. The comprehensive haplotype was constructed by placing in a row the alleles of the 8 loci in the following order: DYS19, DYS388, DYS389A, DYS389B, DYS390, DYS391, DYS392, DYS393.

In this Example, the distinction between relatives and non-relatives is based on the statements provided by the sample donors.

Relatives.

The group of relatives allowed for the analysis of 25 reproduction cycles (A father having a son comprises one reproduction cycle). All relatives showed the same Y chromosome haplotype. Independently from the samples reported above, the inheritance of the Y chromosome haplotype was confirmed in 12 trios father-mother-son for which the paternity was confirmed by the analysis of autosomal polymorphic loci (probability of paternity >99.9%).

TABLE I

TRIESTE

| N | Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 1 | Balbi-1 | | 4 | 1 | 3 | 5 | 5 | 3 | 1 | 2 | 41,355,312 |
| 2 | Balbi-2 | | 3 | 3 | 3 | 6 | 1 | 2 | 1 | 2 | 33,361,212 |
| 3 | Baldassi-1 | | 3 | 1 | 3 | 5 | 2 | 2 | 1 | 3 | 31,352,213 |
| 4 | Baldassi-2 | | 2 | 2 | 2 | 5 | 1 | 2 | 1 | 2 | 22,251,212 |
| 5 | Barut-1 | | 3 | 1 | 3 | 5 | 5 | 3 | 1 | 2 | 31,355,312 |
| 6 | Barut-2 | | 3 | 1 | 3 | 5 | 5 | 3 | 1 | 2 | 31,355,312 |
| 7 | Bencich-1 | | 2 | 3 | 3 | 6 | 2 | 3 | 2 | 2 | 23,362,322 |
| 8 | Bencich-2 | | 2 | 1 | 2 | 6 | 2 | 3 | 1 | 2 | 21,262,312 |
| 9 | Bertocchi-1 | | 3 | 1 | 3 | 6 | 3 | 3 | 1 | 2 | 31,363,312 |
| 10 | Bertocchi-2 | | 4 | 1 | 3 | 6 | 3 | 2 | 1 | 2 | 41,363,212 |
| 11 | Bonazza-1 | | 3 | 2 | 3 | 8 | 3 | 3 | 1 | 2 | 32,353,312 |
| 12 | Bonazza-2 | | 3 | 2 | 3 | 7 | 3 | 3 | 1 | 2 | 32,373,312 |
| 13 | Bugliano-1 | father | 2 | 1 | 3 | 5 | 4 | 2 | 2 | 2 | 21,354,222 |
| 14 | Bugliano-2 | son | 2 | 1 | 3 | 5 | 4 | 2 | 2 | 2 | 21,354,222 |
| 15 | Cociani-1 | | 4 | 1 | 4 | 7 | 5 | 3 | 1 | 2 | 41,475,312 |
| 16 | Cociani-2 | | 3 | 1 | 3 | 6 | 5 | 3 | 1 | 2 | 31,365,312 |
| 17 | Colautti-1 | | 1 | 1 | 3 | 6 | 2 | 2 | 1 | 2 | 11,362,212 |
| 18 | Colautti-2 | | 2 | 3 | 2 | 5 | 2 | 2 | 1 | 4 | 23,252,214 |
| 19 | Coronica-1 | | 2 | 1 | 3 | 5 | 1 | 3 | 2 | 2 | 21,351,322 |
| 20 | Coronica-2 | | 4 | 1 | 3 | 6 | 5 | 2 | 1 | 2 | 41,365,212 |
| 21 | Coslovich-1 | | 4 | 1 | 3 | 6 | 5 | 3 | 1 | 2 | 41,365,312 |
| 22 | Coslovich-2 | | 4 | 1 | 3 | 6 | 5 | 3 | 1 | 2 | 41,365,312 |
| 23 | Degrassi-1 | brother | 3 | 2 | 3 | 8 | 1 | 2 | 1 | 4 | 32,381,214 |
| 24 | Degrassi-2 | | 2 | 1 | 3 | 5 | 2 | 2 | 2 | 2 | 21,352,222 |
| 25 | Degrassi-3 | brother | 3 | 2 | 3 | 8 | 1 | 2 | 1 | 4 | 32,331,214 |
| 26 | Degrassi-4 | | 3 | 2 | 3 | 8 | 1 | 2 | 1 | 4 | 32,381,214 |
| 27 | Degrassi-5 | | 4 | 1 | 3 | 5 | 5 | 3 | 1 | 4 | 41,355,314 |
| 28 | Degrassi-6 | | 3 | 2 | 3 | 8 | 1 | 2 | 1 | 4 | 32,381,214 |
| 29 | Denich-1 | | 4 | 2 | 3 | 7 | 3 | 3 | 1 | 2 | 42,373,312 |
| 30 | Denich-2 | | 4 | 2 | 3 | 7 | 3 | 3 | 1 | 2 | 42,373,312 |
| 31 | Doglia-1 | | 4 | 2 | 2 | 5 | 4 | 3 | 1 | 2 | 42,254,312 |
| 32 | Doglia-2 | | 4 | 2 | 2 | 5 | 4 | 3 | 1 | 2 | 42,254,312 |
| 33 | Doz-1 | | 2 | 1 | 4 | 7 | 4 | 3 | 2 | 1 | 21,474,321 |
| 34 | Doz-2 | | 2 | 1 | 4 | 7 | 4 | 3 | 2 | 1 | 21,474,321 |
| 35 | Ellero-1 | | 4 | 2 | 3 | 6 | 3 | 2 | 1 | 2 | 42,363,212 |
| 36 | Ellero-2 | | 4 | 2 | 3 | 6 | 3 | 2 | 1 | 2 | 42,363,212 |
| 37 | Ferluga-1 | | 4 | 5 | 2 | 5 | 3 | 2 | 1 | 1 | 45,253,211 |
| 38 | Ferluga-2 | | 4 | 5 | 2 | 5 | 3 | 2 | 1 | 1 | 45,253,211 |
| 39 | Filippi-1 | | 4 | 1 | 3 | 5 | 3 | 2 | 1 | 2 | 41,353,212 |
| 40 | Filippi-2 | | 2 | 3 | 2 | 5 | 2 | 2 | 1 | 2 | 23,252,212 |
| 41 | Fontanot-1 | | 2 | 1 | 3 | 5 | 3 | 2 | 2 | 3 | 21,353,223 |
| 42 | Fontanot-2 | | 2 | 1 | 3 | 5 | 3 | 2 | 2 | 3 | 21,353,223 |
| 43 | Fontanot-3 | | 2 | 1 | 3 | 5 | 3 | 2 | 2 | 3 | 21,353,223 |
| 44 | Grassi-1 | | 3 | 2 | 3 | 8 | 1 | 2 | 1 | 4 | 32,381,214 |
| 45 | Grassi-2 | | 4 | 1 | 3 | 5 | 5 | 3 | 2 | 2 | 41,355,322 |
| 46 | Grasso-1 | | 2 | 4 | 3 | 5 | 2 | 3 | 1 | 1 | 24,352,311 |
| 47 | Grasso-2 | | 2 | 1 | 2 | 5 | 1 | 2 | 1 | 2 | 21,251,212 |
| 48 | Kaiser-1 | son | 4 | 2 | 3 | 7 | 4 | 3 | 1 | 2 | 42,374,312 |
| 49 | Kaiser-2 | father | 4 | 2 | 3 | 7 | 4 | 3 | 1 | 2 | 42,374,312 |
| 50 | Kaiser-3 | son | 4 | 2 | 3 | 7 | 4 | 3 | 1 | 2 | 42,374,312 |
| 51 | Maranzana-1 | brother | 2 | 1 | 3 | 5 | 4 | 2 | 2 | 2 | 21,354,222 |
| 52 | Maranzana-2 | brother | 2 | 1 | 3 | 5 | 4 | 2 | 2 | 2 | 21,354,222 |
| 53 | Marcusa-1 | | 2 | 1 | 3 | 5 | 1 | 3 | 2 | 2 | 21,351,322 |
| 54 | Marcusa-2 | | 2 | 1 | 3 | 5 | 1 | 3 | 2 | 2 | 21,351,322 |
| 55 | Medos-1 | | 4 | 2 | 4 | 7 | 3 | 3 | 1 | 2 | 42,473,312 |
| 56 | Medos-2 | | 4 | 2 | 4 | 7 | 3 | 3 | 1 | 2 | 42,473,312 |
| 57 | Pacorini-1 | father | 2 | 4 | 3 | 5 | 1 | 2 | 1 | 1 | 24,351,211 |
| 58 | Pacorini-2 | son | 2 | 4 | 3 | 5 | 1 | 2 | 1 | 1 | 24,351,211 |
| 59 | Parovel-1 | | 2 | 1 | 4 | 6 | 3 | 3 | 2 | 2 | 21,463,322 |
| 60 | Parovel-2 | | 2 | 1 | 4 | 6 | 3 | 3 | 2 | 2 | 21,463,322 |
| 61 | Parovel-3 | | 2 | 1 | 4 | 6 | 3 | 3 | 2 | 2 | 21,463,322 |
| 62 | Pitacco-1 | | 4 | 1 | 3 | 6 | 5 | 2 | 1 | 2 | 41,365,212 |
| 63 | Pitacco-2 | | 4 | 1 | 3 | 6 | 5 | 2 | 1 | 2 | 41,365,212 |
| 64 | Poropat-1 | | 4 | 1 | 3 | 7 | 5 | 2 | 1 | 2 | 41,375,212 |
| 65 | Poropat-2 | | 2 | 4 | 3 | 5 | 3 | 3 | 1 | 1 | 24,353,311 |
| 66 | Radovich-1 | father | 2 | 2 | 3 | 6 | 4 | 3 | 1 | 2 | 22,364,312 |
| 67 | Radovich-2 | son | 2 | 2 | 3 | 6 | 4 | 3 | 1 | 2 | 22,364,312 |
| 68 | Rondi-1 | son | 2 | 1 | 3 | 5 | 4 | 3 | 2 | 1 | 21,354,321 |
| 69 | Rondi-2 | father | 2 | 1 | 3 | 5 | 4 | 3 | 2 | 1 | 21,354,321 |
| 70 | Ruzzier-1 | son | 3 | 4 | 3 | 5 | 3 | 2 | 2 | 1 | 34,353,221 |
| 71 | Ruzzier-2 | father | 3 | 4 | 3 | 5 | 3 | 2 | 2 | 1 | 34,353,221 |
| 72 | Ruzzier-3 | | 3 | 3 | 3 | 5 | 3 | 2 | 2 | 1 | 33,353,221 |
| 73 | Ruzzier-4 | | 3 | 4 | 3 | 5 | 3 | 2 | 2 | 1 | 34,353,221 |
| 74 | Ruzzier-5 | | 3 | 2 | 2 | 5 | 4 | 3 | 3 | 2 | 32,254,332 |

TABLE I-continued

TRIESTE

| N | Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 75 | Sain-1 | | 2 | 2 | 4 | 7 | 2 | 2 | 1 | 1 | 22,472,211 |
| 76 | Sain-2 | | 4 | 1 | 3 | 5 | 5 | 3 | 1 | 2 | 41,355,312 |
| 77 | Savi-1 | | 3 | 1 | 3 | 5 | 5 | 2 | 1 | 2 | 31,355,212 |
| 78 | Savi-2 | | 3 | 1 | 3 | 5 | 5 | 2 | 1 | 2 | 31,355,212 |
| 79 | Sincovich-1 | | 4 | 2 | 5 | 6 | 4 | 3 | 1 | 2 | 42,564,312 |
| 80 | Sincovich-2 | | 3 | 2 | 5 | 5 | 4 | 3 | 2 | 2 | 32,554,322 |
| 81 | Skabar-1 | | 5 | 2 | 3 | 8 | 4 | 3 | 1 | 2 | 52,384,312 |
| 82 | Skabar-2 | | 5 | 2 | 3 | 8 | 4 | 3 | 1 | 2 | 52,384,312 |
| 83 | Spinelli-1 | | 3 | 2 | 2 | 8 | 1 | 2 | 1 | 2 | 32,281,212 |
| 84 | Spinelli-2 | | 2 | 2 | 2 | 4 | 3 | 3 | 1 | 1 | 22,243,311 |
| 85 | Stagni-1 | | 3 | 4 | 3 | 8 | 3 | 2 | 1 | 1 | 34,383,211 |
| 86 | Stagni-2 | | 3 | 3 | 1 | 5 | 2 | 2 | 1 | 2 | 33,152,212 |
| 87 | Tomat-1 | | 2 | 1 | 3 | 6 | 1 | 2 | 2 | 0 | 21,361,220 |
| 88 | Tomat-2 | | 2 | 1 | 4 | 7 | 4 | 3 | 2 | 2 | 21,474,322 |
| 89 | Trani-1 | cousin | 3 | 1 | 3 | 6 | 4 | 3 | 3 | 2 | 31,364,332 |
| 90 | Trani-2 | cousin | 3 | 1 | 3 | 6 | 4 | 3 | 3 | 2 | 31,364,332 |
| 91 | Ulcigrai-1 | | 4 | 1 | 3 | 8 | 5 | 3 | 1 | 2 | 41,385,312 |
| 92 | Ulcigrai-2 | | 4 | 1 | 3 | 8 | 5 | 3 | 1 | 2 | 41,385,312 |
| 93 | Vecchiet-1 | | 2 | 1 | 3 | 8 | 4 | 3 | 1 | 2 | 21,384,312 |
| 94 | Vecchiet-2 | | 2 | 1 | 3 | 8 | 4 | 3 | 1 | 2 | 21,384,312 |
| 95 | Zerial-1 | | 4 | 1 | 3 | 6 | 4 | 2 | 1 | 2 | 41,364,212 |
| 96 | Zerjal-1 | | 4 | 1 | 3 | 8 | 4 | 2 | 1 | 2 | 41,384,212 |
| 97 | Zocchi-1 | | 2 | 1 | 3 | 6 | 5 | 3 | 2 | 2 | 21,365,322 |
| 98 | Zocchi-2 | | 2 | 1 | 3 | 6 | 5 | 3 | 2 | 1 | 21,365,321 |
| 99 | Zoch-1 | | 2 | 1 | 3 | 6 | 5 | 3 | 2 | 2 | 21,365,322 |
| 100 | Zoch-2 | | 3 | 1 | 3 | 6 | 5 | 3 | 2 | 2 | 31,365,322 |
| 101 | Zolle-1 | brother | 3 | 2 | 2 | 6 | 1 | 2 | 1 | 3 | 32,261,213 |
| 102 | Zolle-2 | brother | 3 | 2 | 2 | 6 | 1 | 2 | 1 | 3 | 32,261,213 |
| 103 | Zonta-1 | | 5 | 1 | 3 | 8 | 5 | 2 | 1 | 2 | 51,385,212 |
| 104 | Zonta-2 | | 5 | 1 | 3 | 8 | 5 | 2 | 1 | 2 | 51,385,212 |
| 105 | Zoratto-1 | | 2 | 1 | 2 | 5 | 3 | 2 | 2 | 2 | 21,253,222 |
| 106 | Zoratto-2 | | 2 | 1 | 2 | 5 | 3 | 2 | 2 | 2 | 21,253,222 |

Unrelated People Sharing the Same Surname.

Haplotypes (191) from unrelated people with 49 different surnames were analyzed. People with the same surname frequently shared the same haplotype. The coincidence between haplotype and surname was observed in 171 cases over 624 comparisons (25.2%). Considerable differences were observed between the samples of Trieste and the samples of Friuli as reported in Tables A–E.

TABLE II

| | Coincidence % | |
|---|---|---|
| Place | Unrelated + relatives | Unrelated only |
| Trieste | 57.1 | 48.2 |
| Friuli | 25.2 | 25.0 |
| Total | 28.7 | 27.4 |

The reason for the different percentages observed in Table II between Trieste and Friuli can be easily understood if historical and geographic parameters are considered. In fact, starting in 1730, the population of the town of Trieste grew from 4,000 inhabitants to 104,707 in 1857, due to immigration from the former Austro-Hungarian Empire. Since then, the low number of generations did not allow for the introduction of many discrepancies in surname or haplotype. On the contrary the population of Friuli grew steadily through many centuries; however, immigration, after the Middle Ages, was very limited. Moreover the province of Trieste has an area of 212 km$^2$ while the province of Udine (Friuli) has an area of 4,900 km$^2$. Accordingly, the sampling on a larger territory increases the probabilities of encountering families which diverged long ago or belong to different groups within a polyphyletic surname.

Unrelated People with Different Surnames.

People with different surnames showed different haplotypes. Rare cases of people with different surnames but identical haplotypes were observed: 32 cases over 21,704 comparisons. (p=0.00174). The variability of the Y chromosome haplotype was very high even within the same town.

The low probability of finding two people with a different surname but identical haplotype is even more impressive when it is taken into account that the territory considered in this study is relatively small. Trieste and Udine (Friuli) are 80 Km apart, thus, the diffusion of certain frequent haplotypes could be expected.

Grouping Relatives and Non-relatives.

The distinction between relatives and unrelated people in Table II was based on the statements of the sample donors. Unfortunately, the memory of a common ancestor is easily lost. In fact, common knowledge of kin rarely goes beyond the knowledge of second degree cousins or great grandfather. Nearly one third of the interviewed people (about 2,000) did not remember the name of their paternal grandfather. The study of Y chromosome haplotypes offers a reliable method for identifying kin in male line beyond the circle of the close relatives.

On the basis of surnames and Y chromosome haplotypes, males can be classified into 4 categories.

1) Men differing for both surname and Y haplotype. This group comprises all those who are truly unrelated, both genetically and by registration.

2) The vast majority of people differing for the surname but sharing the same Y haplotype must be considered unrelated. The coincidence of haplotype could be due purely to chance or adoption, natural paternity, registration under the mother's surname, etc. In any case, this haplotype coincidence is rather rare.

The blood or finger nail donors were interviewed a second time to establish possible kinship.

Genealogical Tree of the Miani Gens of Friuli.

Table A sets forth the haplotypes of the 11 people with the surname Miani from Friuli.

TABLE A

| N | Surname | Relative | DYS 19 | DYS 388 | DYS 389A | DYS 389B | DYS 390 | DYS 391 | DYS 392 | DYS 393 | Haplotype |
|---|---------|----------|--------|---------|----------|----------|---------|---------|---------|---------|-----------|
| 65 | Miani-01 |  | 2 | 1 | 4 | 5 | 2 | 2 | 2 | 2 | 21,452,222 |
| 66 | Miani-02 |  | 2 | 1 | 4 | 5 | 2 | 3 | 2 | 3 | 21,452,323 |
| 67 | Miani-03 |  | 3 | 2 | 4 | 5 | 2 | 2 | 1 | 4 | 32,452,214 |
| 68 | Miani-04 |  | 2 | 1 | 3 | 6 | 0 | 2 | 1 | 3 | 21,360,213 |
| 69 | Miani-05 |  | 2 | 1 | 4 | 5 | 1 | 3 | 2 | 3 | 21,451,323 |
| 70 | Miani-06 |  | 2 | 3 | 3 | 6 | 1 | 2 | 1 | 3 | 23,361,213 |
| 71 | Miani-07 |  | 3 | 2 | 4 | 5 | 2 | 2 | 1 | 4 | 32,452,214 |
| 72 | Miani-08 |  | 4 | 1 | 4 | 6 | 3 | 2 | 1 | 2 | 41,463,212 |
| 73 | Miani-09 |  | 2 | 1 | 4 | 5 | 3 | 3 | 2 | 2 | 21,453,322 |
| 74 | Miani-10 |  | 2 | 3 | 3 | 6 | 1 | 2 | 1 | 3 | 23,361,213 |
| 75 | Miani-11 |  | 3 | 2 | 4 | 5 | 1 | 2 | 1 | 3 | 32,451,213 |

3) Men differing for the Y chromosome haplotype but sharing the same surname cannot be considered related by male lineage. The major source of surname coincidence is the polyphyletic origin of surnames but a contribution is surely introduced by non-paternity or adoption, etc. Also included in this group are those non-infrequent cases of haplotypes differing only for 1 locus over 8 analysed loci. This particular case will be treated in the next section.
4) The people sharing both surname and Y chromosome haplotype can be considered relatives even if they do not recognise themselves as such. In fact, the probability of sharing both characteristics by chance is given by the product of the two odds and therefore must be considerably lower than the probability calculated for different surnames and equal haplotype (p=0.00174). Reversing this concept, it is observed that the people sharing the Y haplotype and the surname have greater than 99.8% probability of sharing a common male ancestor who lived during the last 2–3 centuries.

Some members of a group with the same surname can show a haplotypes differing for a single locus. Most probably these variants are mutations and are the expression of a relatively recent divergence from an original haplotype, that is, they represent a different branch of a group of kin. The research group of Cavalli-Sforza reported (Goldstain et al., (1995) PNAS 92:6723–27) a method for genetic absolute dating based on microsatellites. Accepting the reported average mutation rate of 0.0056 and considering that the haplotypes analyzed were constructed on 8 loci, a variant haplotype for a single locus would be expected every 22 generations. Therefore two contemporary people with the same surname and divergent Y haplotype for one locus could share a common ancestor who lived about 2–3 centuries ago (11 generations ago).

EXAMPLE II

Province Level Sampling:

About 1300 blood or fingernail samples were collected in the town and province of (Friuli) with the same criteria that was adopted for Trieste. The 9 most frequent surnames were chosen for a more extended study and additional samples were collected to provide 9–15 people for each surname.

Applying the rules described in the previous example, it is possible to construct a dendrogram connecting the 9 different haplotypes. The numbers in the dendrogram refer to the different Miani as reported in Table A. Identical haplotypes are localized in the same place, separated by comas.

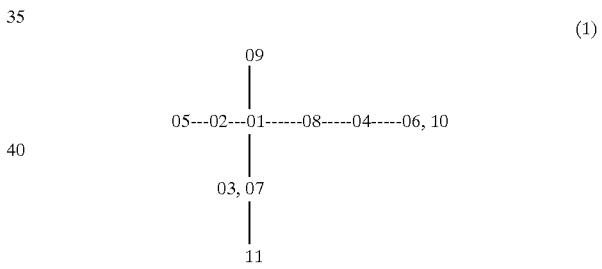

(1)

The dendrogram illustrated above is justified by 21 mutations, however, a different "tree" may be constructed maintaining the minimum number of 21 mutations:

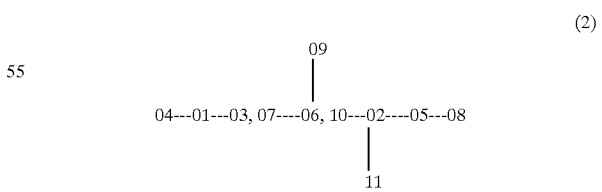

(2)

The Miani dendrogram can be modified to visualize the number of mutations involved in the passage from one haplotype to the other by proportional connections. Thus dendrogram (1) may be further modified as shown below:

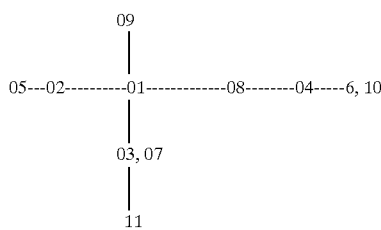

(3)

The last dendrogram can be used for constructing the final "Genealogical Tree" of the Gens Miani. This involves defining the base or roots, trunk and branches. Any of the branches of the dendrogram can be used as the trunk but for aesthetic reasons it is convenient to chose the longest branch. Once the trunk is fixed, the rest of the tree can be constructed changing the angle of the branches of the dendrogram to obtain a tree shape. The samples will be localised on the trunk and on branches, maintaining the proportional distances of dendrogram (3) shown above (Goldstain et al., (1995) PNAS 92:6723–6727). Alternatively, the Genealogical Tree could report the places of residence of the donors or the complete haplotype or the name of the donors. Finally, for aesthetic reasons, the Tree can be finished adding leaves and small branches.

Figure 2:
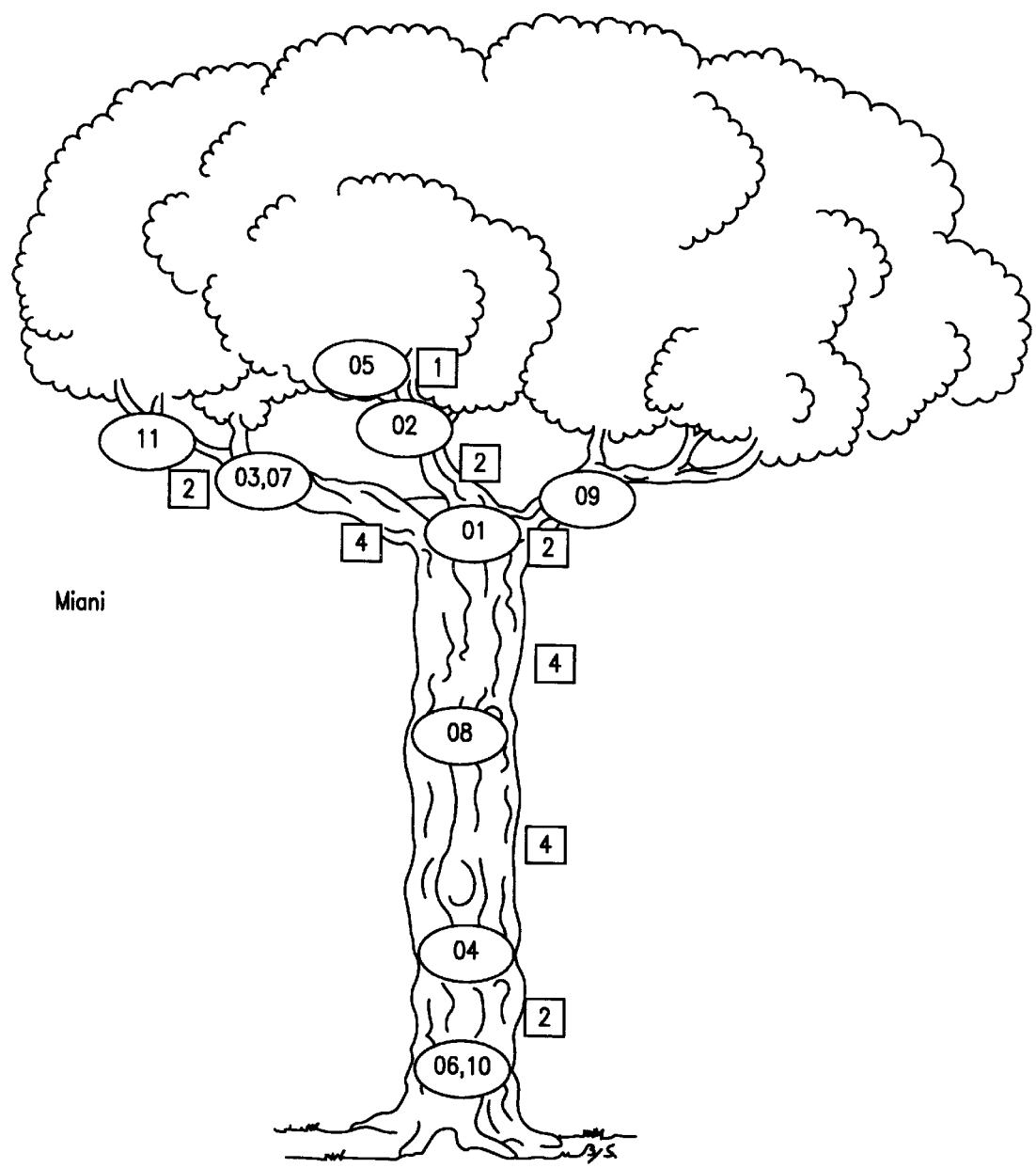
FIG. 2 is a schematic representation of the Miani genealogical tree. The number of mutations required to pass from one haplotype to another is shown in the square boxes. The numbers in ovals correspond to the individuals set forth in Table A.

FIG. 2 depicts the Genealogical Tree of the Miani family. The numbers in ovals refer to the Miani as numbered in Table A above. The number of mutations required to pass from one haplotype to another are reported in the square boxes. The following information can be obtained from the above analysis of Y chromosome polymorphisms:

1) Relatives: Miani06 and Miani10 have the same haplotype and it is highly probable that they share a recent common ancestor who lived in the last 2 centuries. They can be considered relatives even if they do not recognise themselves as such. The same consideration is valid for Miani03 and Miani07.

2) Far relatives: Miani02 and Miani05 differ for only one locus, most probably they share a common ancestor who lived 2–3 centuries ago. Those differing for 2 loci can be considered as very distant relatives (Miani 01/02; 01/09; 11/03,07; 04/06,10) suggesting that the common ancestor lived 4–6 centuries ago.

3) Unrelated: All the remaining Miani can be considered unrelated either because they diverged too many centuries ago or because the coincidence of a few loci is purely due to chance.

The high haplotype variability of the Miani is justified by the polyphyletic origin of this surname. In some cases the surname was derived from the Roman cognomen Aemilianus and, more frequently, it designated an origin from Emilia.

Genealogical Tree of the Bassi Gens of Friuli.

Table B shows the haplotypes of the Bassis of Friuli:

TABLE B

| N | Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 1 | Bassi-01 | 2nd Cousin | 2 | 1 | 3 | 5 | 4 | 3 | 3 | 1 | 21,354,331 |
| 2 | Bassi-02 | | 3 | 1 | 3 | 4 | 3 | 3 | 3 | 2 | 31,343,332 |
| 3 | Bassi-03 | | 2 | 1 | 3 | 4 | 4 | 3 | 3 | 1 | 21,344,331 |
| 4 | Bassi-04 | | 3 | 1 | 2 | 3 | 2 | 5 | 3 | 2 | 31,232,532 |
| 5 | Bassi-05 | | 3 | 4 | 2 | 4 | 3 | 2 | 2 | 1 | 34,243,221 |
| 6 | Bassi-06 | 2nd Cousin | 2 | 1 | 3 | 5 | 4 | 3 | 3 | 1 | 21,354,331 |
| 7 | Bassi-07 | | 2 | 1 | 3 | 5 | 4 | 3 | 3 | 1 | 21,354,331 |
| g | Bassi-08 | | 2 | 3 | 2 | 4 | 1 | 2 | 2 | 2 | 23,241,222 |
| 9 | Bassi-09 | | 3 | 1 | 2 | 5 | 2 | 3 | 3 | 2 | 31,252,332 |
| 10 | Bassi-10 | | 2 | 1 | 3 | 5 | 2 | 3 | 3 | 2 | 21,352,332 |
| 11 | Bassi-11 | | 2 | 1 | 3 | 5 | 4 | 3 | 3 | 1 | 21,354,331 |
| 12 | Bassi-12 | | 3 | 1 | 3 | 4 | 3 | 3 | 3 | 2 | 31,343,332 |

As illustrated above for the Miani, a dendrogram may be constructed for the Bassi:

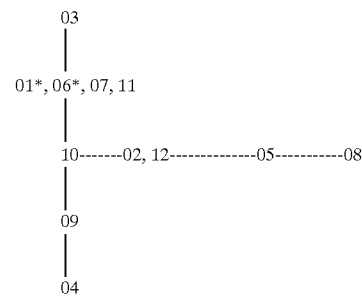

Figure 3:
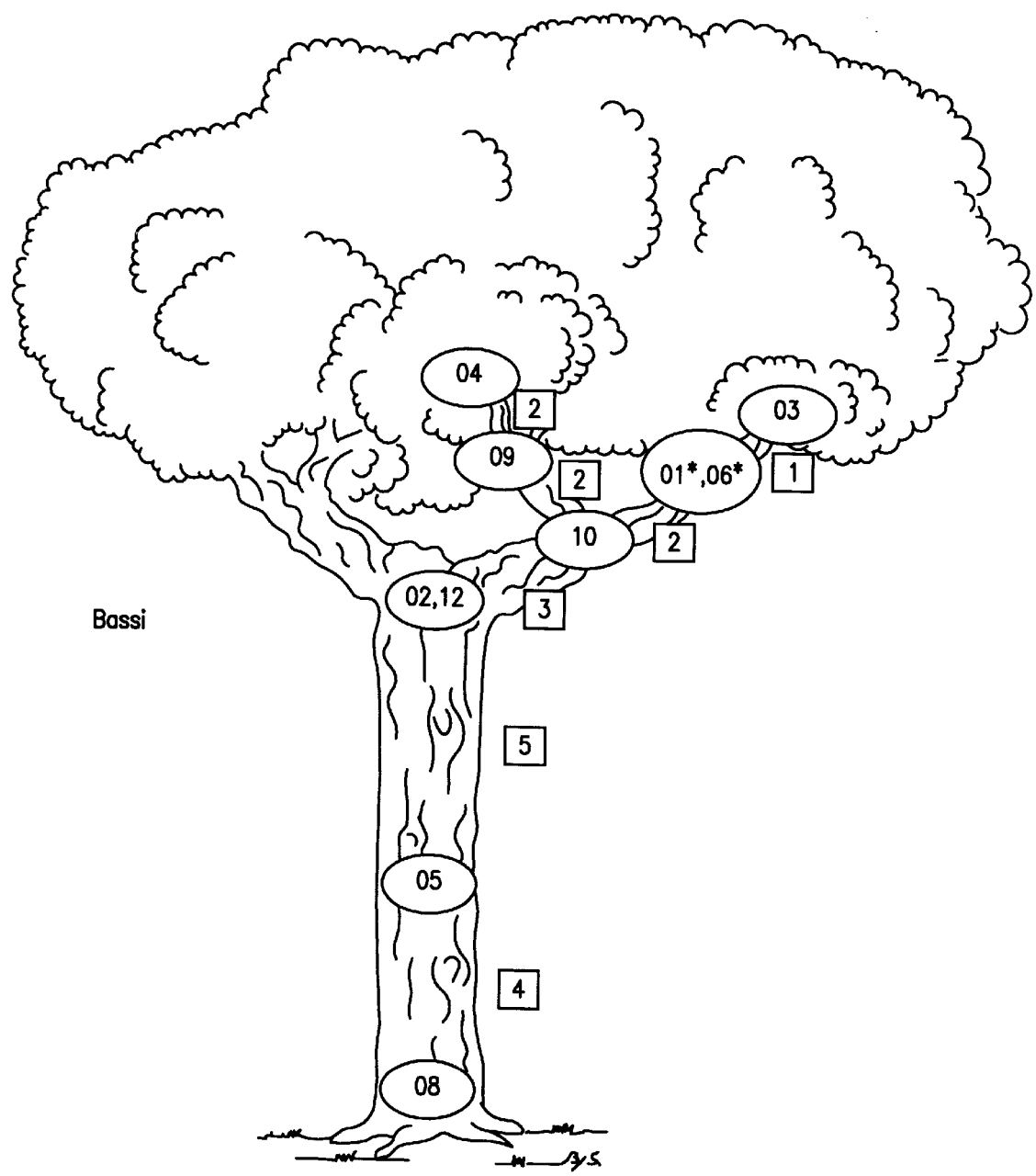
FIG. 3 is a schematic representation of the Bassi genealogical tree. The number of mutations required to pass from one haplotype to another is shown in the square boxes. The numbers in ovals correspond to the individuals set forth in Table B.

The numbers in the dendrogram refer to the different Bassi as reported in Table B. Indentical haplotypes are localized in the same place, separated by commas. The two samples with the asterisks are 2nd degree cousins. The results of the analysis of the Bassi Y chromosome polymorphisms are depicted in FIG. 3 and described below:

1) Relatives: Bassi 01, 06, 07 and 11 share a relatively recent common ancestor and therefore they can be considered relatives even if only Bassi 01 and Bassi 06 recognised themselves as 2nd degree cousins. The same consideration is valid for Bassi 02 and Bassi 12.
2) Distant relatives: Bassi 03 differs for only one locus from the main group of the Bassi, most probably they share a common ancestor who lived less than 2–3 centuries ago. Those differing for 2 loci can be considered as very distant relatives (Bassi 10/01*,06*,07,11; Bassi 10/09; Bassi 09/04) sharing a relative who lived 4–6 centuries ago.
3) Unrelated: All the remaining Bassi can be considered unrelated.

The Bassi surname refers to short stature, it is common all over Italy and is of polyphyletic origin. It is interesting to note that there is a substantial group of 8 people that can be considered relatives of far relatives (left side of the dendrogram).

Genealogical Tree of the Beltrame Gens of Friuli

The haplotypes of the Beltrame are reported in Table C.

Figure 4:
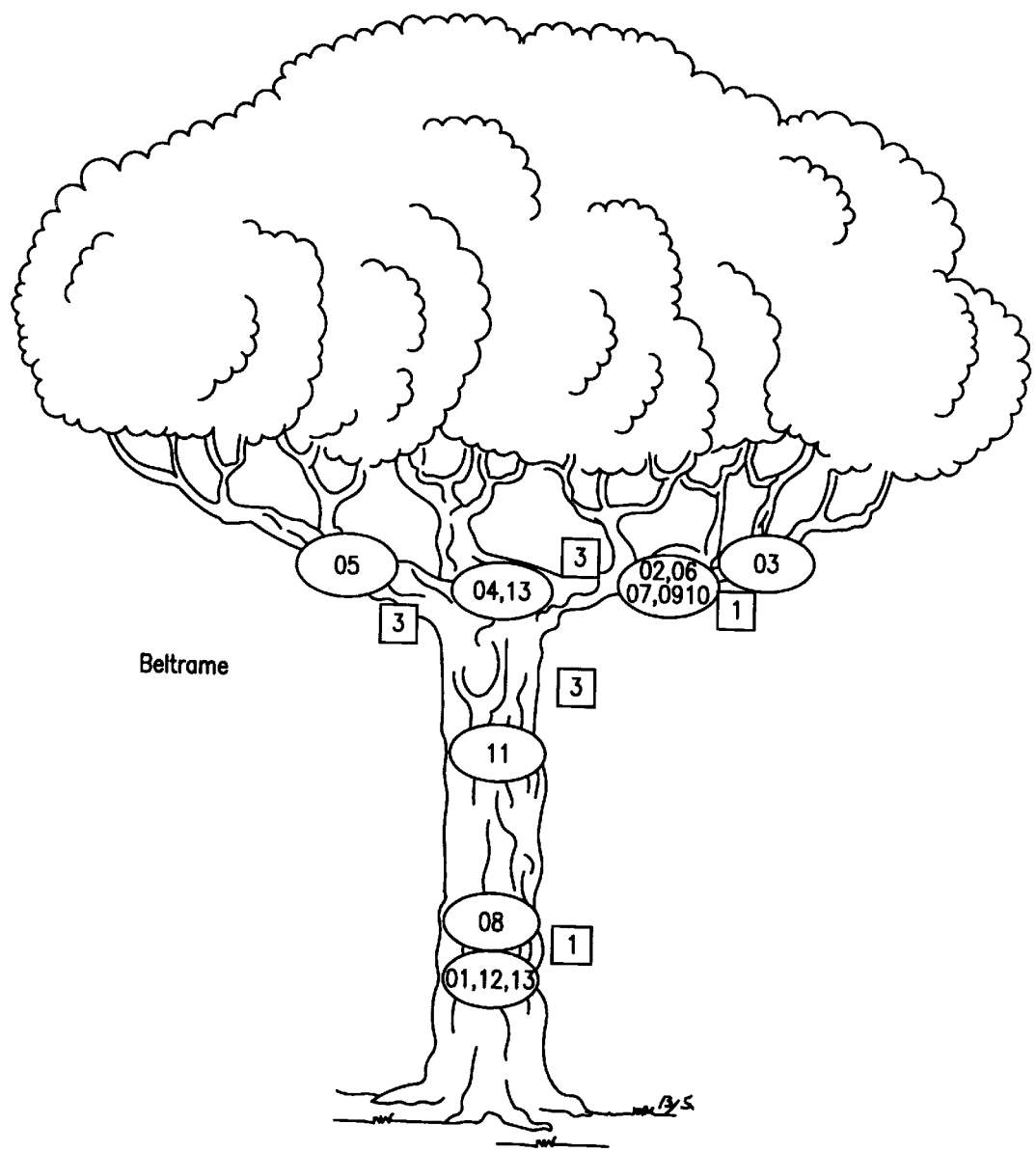
FIG. 4 is a schematic representation of the Beltrame genealogical tree. The number of mutations required to pass from one haplotype to another is shown in the square boxes. The numbers in ovals correspond to the individuals set forth in Table C.

The genealogical tree derived from these data is depicted in FIG. 4.

1) Relatives: Beltrame 02, 06, 07, 09 and 10 share a recent common ancestor who lived less than 2 centuries ago and therefore they can be considered relatives even if they do not recognise themselves as such. The same consideration is valid for Beltrame 04, 13 and Beltrame 01, 12 and 14.
2) Distant relatives: Beltrame 03 differs for only one locus from the main group of the Beltrame. It is likely they share a common ancestor who lived some 2–3 centuries ago. The same consideration is valid for Beltrame 08 and the group at the base of the tree.
3) Unrelated: All the remaining Beltrame can be considered unrelated.

TABLE C

| N | Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 13 | Beltrame-01 | | 2 | 1 | 2 | 4 | 3 | 4 | 2 | 1 | 23,633,421 |
| 14 | Beltrame-02 | | 4 | 1 | 3 | 5 | 4 | 2 | 1 | 2 | 43,774,212 |
| 15 | Beltrame-03 | | 5 | 1 | 3 | 5 | 4 | 2 | 1 | 2 | 53,774,212 |
| 16 | Beltrame-04 | | 2 | 1 | 3 | 5 | 2 | 2 | 2 | 2 | 23,772,222 |
| 17 | Beltrame-05 | | 2 | 1 | 3 | 5 | 3 | 2 | 1 | 4 | 23,773,214 |
| 18 | Beltrame-06 | | 4 | 1 | 3 | 5 | 4 | 2 | 1 | 2 | 43,774,212 |
| 19 | Beltrame-07 | | 4 | 1 | 3 | 5 | 4 | 2 | 1 | 2 | 43,774,212 |
| 20 | Beltrame-08 | | 2 | 1 | 2 | 4 | 3 | 3 | 2 | 1 | 23,633,321 |
| 21 | Beltrame-09 | | 4 | 1 | 3 | 5 | 4 | 2 | 1 | 2 | 43,774,212 |
| 22 | Beltrame-10 | | 4 | 1 | 3 | 5 | 4 | 2 | 1 | 2 | 43,774,212 |
| 23 | Beltrame-11 | | 2 | 1 | 3 | 5 | 4 | 3 | 2 | 1 | 23,774,321 |
| 24 | Beltrame-12 | | 2 | 1 | 2 | 4 | 3 | 4 | 2 | 1 | 23,633,421 |
| 25 | Beltrame-13 | | 2 | 1 | 3 | 5 | 2 | 2 | 2 | 2 | 23,772,222 |
| 26 | Beltrame-14 | | 2 | 1 | 2 | 4 | 3 | 4 | 2 | 1 | 23,633,421 |

The dendrogram generated from this data includes 14 samples and 7 haplotypes. The numbers in the dendrogram below refer to the different Beltrame as reported in Table C. Identical haplotypes are localized in the same place, separated by comas.

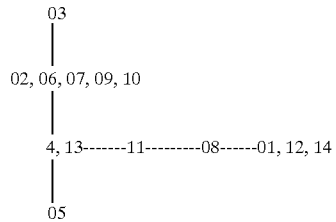

The Beltrame surname is common in North Italy. It appeared in the Middle Ages as a derivation from the Franco-German name Beltramo. The ancient origin of this surname allowed both for a substantial divergence of the Gens and for the polyphyletic origin. Notably the Beltrame Gens shows two clusters of relatives or distant relatives at the ends of the two main branches. Frequently the haplotypes diverging for one locus only are connected with the largest group sharing the same haplotype.

The Genealogical Tree of the Deganos of Friuli

The haplotypes of the Deganos are depicted in Table D.

TABLE D

| N | Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 27 | Degano-01 | | 2 | 2 | 2 | 3 | 1 | 2 | 1 | 1 | 22,231,211 |
| 28 | Degano-02 | | 4 | 1 | 3 | 5 | 4 | 2 | 1 | 2 | 41,354,212 |
| 29 | Degano-03 | | 2 | 5 | 3 | 4 | 2 | 2 | 1 | 1 | 25,342,211 |
| 30 | Degano-04 | | 2 | 5 | 3 | 4 | 2 | 2 | 1 | 1 | 25,342,211 |

TABLE D-continued

| N | Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 31 | Degano-05 | | 2 | 5 | 3 | 4 | 2 | 2 | 1 | 1 | 25,342,211 |
| 32 | Degano-06 | | 2 | 1 | 3 | 4 | 3 | 2 | 2 | 1 | 21,343,221 |
| 33 | Degano-07 | | 2 | 2 | 2 | 3 | 1 | 2 | 1 | 1 | 22,231,211 |
| 34 | Degano-08 | | 2 | 2 | 2 | 3 | 1 | 2 | 1 | 1 | 22,231,211 |
| 35 | Degano-09 | | 2 | 5 | 3 | 4 | 2 | 2 | 1 | 1 | 25,342,211 |
| 36 | Degano-10 | | 3 | 1 | 3 | 4 | 4 | 3 | 3 | 3 | 31,344,333 |
| 37 | Degano-11 | | 2 | 5 | 3 | 4 | 2 | 2 | 1 | 1 | 25,342,211 |
| 38 | Degano-12 | | 2 | 5 | 3 | 4 | 2 | 2 | 1 | 1 | 25,342,211 |
| 39 | Degano-13 | | 1 | 1 | 3 | 6 | 3 | 2 | 1 | 2 | 11,363,212 |
| 40 | Degano-14 | | 2 | 2 | 2 | 3 | 1 | 2 | 1 | 1 | 22,231,211 |
| 41 | Degano-15 | | 2 | 1 | 3 | 4 | 2 | 2 | 2 | 2 | 21,342,222 |

The dendrogram shown below includes 15 samples and 7 haplotypes. The numbers in the dendrogram refer to the different Degano as reported in Table D. Identical haplotypes are localised in the same place, separated by comas.

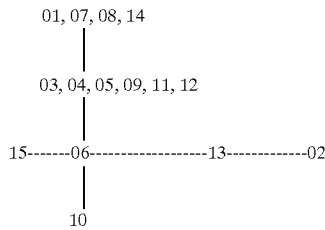

Figure 5:
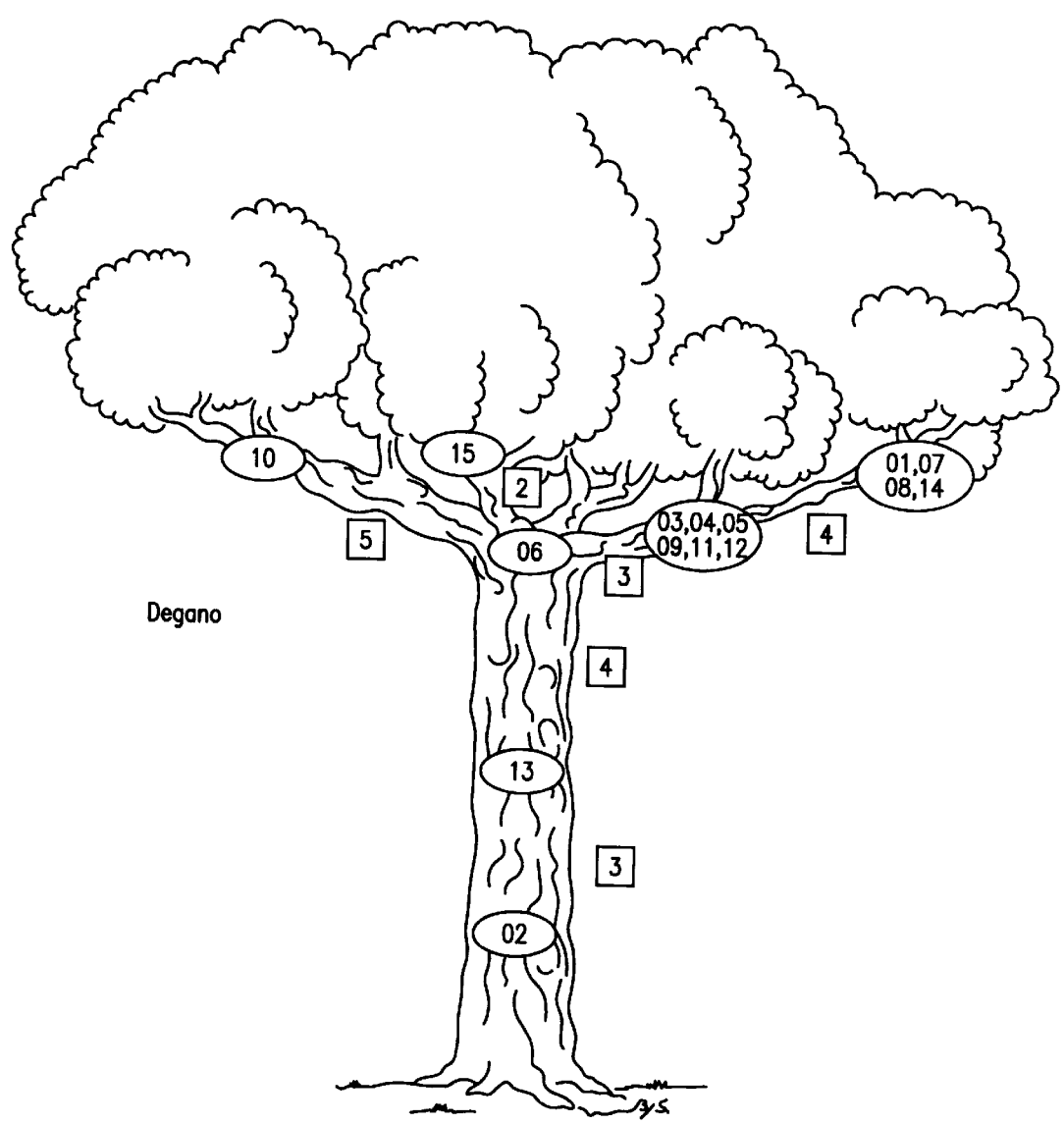
FIG. 5 is a schematic representation of the Degano genealogical tree. The number of mutations required to pass from one haplotype to another is shown in the square boxes. The numbers in ovals correspond to the individuals set forth in Table D.

The genealogical tree of the Deganos is depicted in FIG. 5.

1) Relatives: There are two groups of relatives Degano 01, 07, 08, 14 and Degano 03. 04, 05, 09, 11, 12. Each of the two groups has a common ancestor who lived less than 2–3 centuries ago.
2) Distant relatives: Most probably Degano 06 and 15 share a common ancestor who lived 4–6 centuries ago (two mutations).
3) Unrelated: All the remaining Degano can be considered unrelated.

The Degano surname is specific of Friuli and is derived from the office Decanus (Dean), title of high officials. Since each community had their own Decanus, the Degano Gens have to be considered of polyphyletic origin. The Gens Degano shows two unrelated clusters of relatives.

Genealogical Tree of the Zampas

The Gens Zampa gave the most intriguing result of all surname groups studied. In fact, all the Zampa, 12 people, showed the same haplotype (Table E).

TABLE E

| N | Sample Surname | Relative | DYS 19 | DYS 388 | DYS 389A | DYS 389B | DYS 390 | DYS 391 | DYS 392 | DYS 393 | Haplotype |
|---|---|---|---|---|---|---|---|---|---|---|---|
| 85 | Zampa-01 | | 2 | 2 | 2 | 4 | 2 | 2 | 1 | 2 | 22,242,212 |
| 86 | Zampa-02 | | 2 | 2 | 2 | 4 | 2 | 2 | 1 | 2 | 22,242,212 |
| 87 | Zampa-03 | | 2 | 2 | 2 | 4 | 2 | 2 | 1 | 2 | 22,242,212 |
| 88 | Zampa-04 | | 2 | 2 | 2 | 4 | 2 | 2 | 1 | 2 | 22,242,212 |
| 89 | Zampa-05 | | 2 | 2 | 2 | 4 | 2 | 2 | 1 | 2 | 22,242,212 |
| 90 | Zampa-06 | | 2 | 2 | 2 | 4 | 2 | 2 | 1 | 2 | 22,242,212 |
| 91 | Zampa-07 | | 2 | 2 | 2 | 4 | 2 | 2 | 1 | 2 | 22,242,212 |
| 92 | Zampa-08 | | 2 | 2 | 2 | 4 | 2 | 2 | 1 | 2 | 22,242,212 |
| 93 | Zampa-09 | | 2 | 2 | 2 | 4 | 2 | 2 | 1 | 2 | 22,242,212 |
| 94 | Zampa-10 | | 2 | 2 | 2 | 4 | 2 | 2 | 1 | 2 | 22,242,212 |
| 95 | Zampa-11 | | 2 | 2 | 2 | 4 | 2 | 2 | 1 | 2 | 22,242,212 |
| 96 | Zampa-12 | | 2 | 2 | 2 | 4 | 2 | 2 | 1 | 2 | 22,242,212 |

Figure 6:
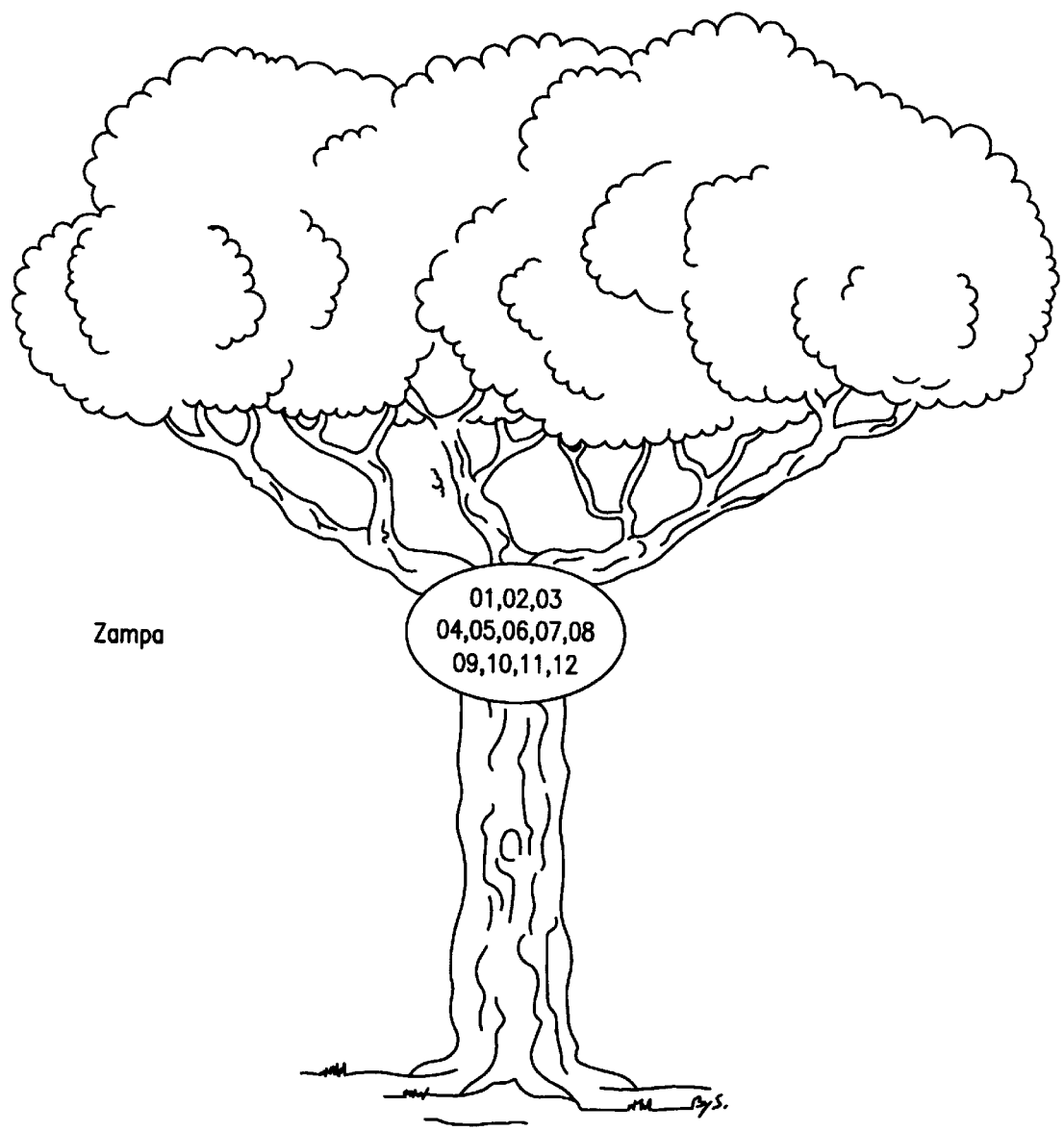
FIG. 6 is a schematic representation of the Zampa genealogical tree. The number of mutations required to pass from one haplotype to another is shown in the square boxes. The numbers in ovals correspond to the individuals set forth in Table E.

In light of this result, these samples were also analysed at autosomal polymorphic loci to demonstrate that they were isolated from different people. The autosomal loci showed normal polymorphism and demonstrated that the 12 samples belonged to 12 different people. As for all the other donors, the Zampa donors were interviewed on their possible kinship and none of them recognised any other Zampa as a known relative. Moreover, the surname Zampa is typical of Friuli, the estimated population in Friuli is around 200–300 people and it is rather uncommon in other parts of Italy. The origin of the surname is a nickname in local dialect meaning left handed people. Both the Y chromosome analyses and data on the surname frequency and distribution are in favour of a monophyletic origin of the Zampa Gens of Friuli, at least those here analysed, and are of relatively recent origin. The peculiar representation of their genealogical tree is shown in FIG. 6.

EXAMPLE III

Nation and Worldwide Sampling

The "Graziosi" surname of Italian origen was chosen for the nation and world-wide studies. In an estimated total male population of about 2,050 males with that surname, finger nail cuts were obtained from 237 people (11% of the total male population), 187 of whom live in Italy. The remaining individuals tested live in France (3), The Netherlands (2), United Kingdom (2), Canada (4), USA (36), Argentina (2)

and Australia (1). In these studies, the following loci were analyzed: DYS19, DYS388, DYS390, DYS391, DYS392, and DYS393. It was possible to establish kinship for some samples but an extensive study on relatedness between individuals is currently in progress. The results are reported in Table III.

TABLE III

| | Sample | DYS19 | DYS388 | DYS390 | DYS391 | DYS392 | DYS393 | haplotype | N. |
|---|---|---|---|---|---|---|---|---|---|
| 1 | R148,155 | 1 | 2 | 2 | 2 | 5 | 3 | 122,253 | 2 |
| 2 | NO2,7 | 1 | 2 | 4 | 2 | 4 | 3 | 124,243 | 2 |
| 3 | AR1,2; U4 | 1 | 2 | 4 | 3 | 1 | 3 | 124,313 | 3 |
| 4 | NA1; PG6; R134 | 1 | 2 | 4 | 3 | 1 | 4 | 124,314 | 3 |
| 5 | R280 | 2 | 2 | 2 | 3 | 1 | 3 | 222,313 | 1 |
| 6 | R157 | 2 | 2 | 2 | 3 | 3 | 3 | 222,333 | 1 |
| 7 | R223 | 2 | 2 | 2 | 4 | 3 | 3 | 222,433 | 1 |
| 8 | C7; NL2,3; U89 | 2 | 2 | 3 | 3 | 1 | 2 | 223,312 | 4 |
| 9 | LQ7,8,10,14,17; MI27; PG15; TO2; U21 | 2 | 2 | 3 | 3 | 1 | 3 | 223,313 | 9 |
| 10 | RT2; VA2 | 2 | 2 | 3 | 3 | 3 | 3 | 223,333 | 2 |
| 11 | R77,125; U117 | 2 | 2 | 3 | 4 | 1 | 3 | 223,413 | 3 |
| 12 | R253 | 2 | 2 | 3 | 4 | 4 | 3 | 223,443 | 1 |
| 13 | R22,34,36 | 2 | 2 | 3 | 5 | 4 | 3 | 223,543 | 3 |
| 14 | R 114 | 2 | 2 | 4 | 3 | 1 | 3 | 224,313 | 1 |
| 15 | GE4; R236; U114 | 2 | 2 | 4 | 3 | 3 | 3 | 224,333 | 3 |
| 16 | R159 | 2 | 2 | 4 | 3 | 5 | 3 | 224,353 | 1 |
| 17 | PS2, R130, U43 | 2 | 2 | 4 | 4 | 1 | 3 | 224,413 | 3 |
| 18 | PG4,11; U51,UK1,2 | 2 | 2 | 4 | 4 | 3 | 3 | 224,433 | 5 |
| 19 | R262 | 2 | 2 | 4 | 4 | 4 | 3 | 224,443 | 1 |
| 20 | PI2 | 2 | 3 | 3 | 3 | 1 | 1 | 233,311 | 1 |
| 21 | R227 | 2 | 4 | 2 | 3 | 1 | 3 | 242,313 | 1 |
| 22 | PE1,8; R66,131 | 2 | 4 | 3 | 3 | 1 | 3 | 243,313 | 4 |
| 23 | PG14; R135,139,290 | 2 | 4 | 4 | 3 | 1 | 2 | 244,312 | 4 |
| 24 | R99 | 2 | 4 | 4 | 4 | 1 | 2 | 244,412 | 1 |
| 25 | R1 | 2 | 5 | 2 | 3 | 3 | 2 | 252,332 | 1 |
| 26 | GE3 | 2 | 6 | 3 | 4 | 1 | 2 | 263,412 | 1 |
| 27 | R221 | 3 | 2 | 1 | 3 | 1 | 4 | 321,314 | 1 |
| 28 | R101 | 3 | 2 | 1 | 3 | 2 | 4 | 321,324 | 1 |
| 29 | R20 | 3 | 2 | 1 | 3 | 3 | 4 | 321,334 | 1 |
| 30 | MC33; MI22,28; U91 | 3 | 2 | 2 | 3 | 1 | 4 | 322,314 | 4 |
| 31 | U49 | 3 | 2 | 2 | 6 | 1 | 1 | 322,611 | 1 |
| 32 | LQ16; MI7; PE16; U3,122 | 3 | 2 | 3 | 4 | 1 | 1 | 323,411 | 5 |
| 33 | MI17 | 3 | 2 | 3 | 4 | 1 | 2 | 323,412 | 1 |
| 34 | MO3,9,20,21,26,27,34,37,38,39,43,53,57,58,60; BO127,130,133,140,144; R152,163; U1,2, | 3 | 2 | 3 | 4 | 3 | 3 | 323,433 | 24 |
| 35 | C14; F3; U111 | 3 | 2 | 4 | 3 | 1 | 2 | 324,312 | 3 |
| 36 | AN2,4,9,10,15,17,20,23, 33,37,49,51; R58,62,166,181,192,257; MI14; PE6,14; PG8; TO4 | 3 | 2 | 4 | 4 | 4 | 3 | 324,443 | 23 |
| 37 | MI21 | 3 | 2 | 5 | 3 | 1 | 2 | 325,312 | 1 |
| 38 | R291 | 3 | 2 | 5 | 4 | 3 | 3 | 325,433 | 1 |
| 39 | FO2; RN1,2,7, 8 ,9,10;PS5; R246; TS1; UD2; VI1 | 3 | 3 | 2 | 3 | 1 | 4 | 332,314 | 12 |
| 40 | R17 | 3 | 3 | 2 | 4 | 1 | 4 | 332,414 | 1 |
| 41 | R79 | 3 | 3 | 3 | 3 | 1 | 2 | 333,312 | 1 |
| 42 | GE2; R206; U101.102 | 3 | 3 | 3 | 4 | 3 | 3 | 333,433 | 4 |
| 43 | U32 | 3 | 3 | 4 | 4 | 1 | 1 | 334,411 | 1 |
| 44 | R241,275,278,293 | 3 | 3 | 4 | 4 | 3 | 3 | 334,433 | 4 |
| 45 | R50 | 3 | 3 | 4 | 5 | 3 | 3 | 334,533 | 1 |
| 46 | R137 | 3 | 3 | 5 | 3 | 3 | 3 | 335,333 | 1 |
| 47 | R146 | 3 | 4 | 2 | 3 | 1 | 4 | 342,314 | 1 |
| 48 | R80 | 3 | 4 | 4 | 3 | 1 | 3 | 344,313 | 1 |
| 49 | R45 | 3 | 4 | 4 | 4 | 1 | 3 | 344,413 | 1 |
| 50 | R3 | 3 | 4 | 4 | 4 | 3 | 3 | 344,433 | 1 |
| 51 | U90 | 3 | 5 | 3 | 1 | 1 | 2 | 353,112 | 1 |
| 52 | CH160; MC18; PE17 | 3 | 5 | 3 | 3 | 1 | 2 | 353,312 | 3 |
| 53 | CO164; MC1,9,11,12,23, 34,37,25; PE7,15; AP57; R28,214,255; U50 | 3 | 5 | 3 | 4 | 1 | 2 | 353,412 | 16 |
| 54 | MI3,6,29.30 | 3 | 5 | 5 | 3 | 1 | 2 | 355,312 | 4 |
| 55 | AU1; TN1 | 3 | 6 | 3 | 4 | 3 | 3 | 363,433 | 2 |
| 56 | RT5 | 4 | 2 | 3 | 3 | 3 | 3 | 423,333 | 1 |
| 57 | CH159,197; GR1; LT3; R150 | 4 | 2 | 3 | 4 | 3 | 3 | 423,433 | 5 |

TABLE III-continued

| Sample | DYS19 | DYS388 | DYS390 | DYS391 | DYS392 | DYS393 | haplotype | N. |
|---|---|---|---|---|---|---|---|---|
| 58 F7 | 4 | 2 | 4 | 4 | 1 | 1 | 424,411 | 1 |
| 59 TE5,9 | 4 | 2 | 4 | 4 | 1 | 4 | 424,414 | 2 |
| 60 R105; U20,23.23s,23n, 23b,96 | 4 | 3 | 3 | 3 | 1 | 1 | 433,311 | 7 |
| 61 BO129,141,151; C6; R244; U-074 | 4 | 6 | 3 | 2 | 1 | 2 | 463,212 | 6 |
| 62 U52; VE1 | 4 | 6 | 3 | 3 | 1 | 3 | 463,313 | 2 |
| 63 PG13;.R96 | 5 | 2 | 1 | 3 | 1 | 4 | 521,314 | 2 |
| 64 F4; U84 | 5 | 2 | 4 | 3 | 1 | 2 | 524,312 | 2 |
| 65 PG9; U37,44 | 5 | 3 | 1 | 4 | 1 | 4 | 531,414 | 3 |
| 66 AV0;1,2,3,4,5,6,7,68,95, 97,99,114,118,119; C3; TS2; U28,30,41,75,103 | 5 | 3 | 3 | 3 | 1 | 1 | 533,311 | 22 |
| 67 NO9 | 5 | 6 | 4 | 2 | 4 | 3 | 564,243 | 1 |
| | | | | | | | Total | 237 |

Legend: Letters refer to places, numbers refer to individuals of a given place. Counties:
AR = Argentina; AU = Australia; C = Canada; F = France; NL = Netherlands; U = USA; UK = United Kingdom. Italian provinces: AN = Ancona; AV = Avellino; BQ = Bologna; CH = Chieti; CO = Como; FO = Forli; GE = Genova; GR = Grosseto; LQ = L'Aquila;
LT = Latina; MC = Macerata; MI = Milano; MO = Modena; NA = Napoli; NO = Novara;
PE = Pescara; PS = Pesaro; PG:Perugia; PI = Pisa; R = Roma; RN = Rimini; RT = Rieti;
TE = Teramo; TN = Trento; TO = Torino; TS = Trieste; UD = Udine; VA = Varese;
VE = Venezia; VI = Vicenza.

The majority of the Graziosis are distributed in Central Italy, between Rome and Modena. The surname includes 67 haplotypes. The most frequent haplotypes, # 34, 36, 53 and 66, show a core of people in a single place and some members dispersed in several places, frequently in large towns. Actually large towns as Roma, Milano and Bologna show a great variety of haplotypes and only a few people sharing the same haplotype. Such a variability could be due to immigration into large towns coupled with the polyphyletic origin of the surname. On the contrary smaller towns, as Modena, Ancona, Macerata, Rimini, Avellino, show only one specific haplotype. Most probably each group descends from one ancestor who colonized the place and, judging by the number of people, this must have occurred a few centuries ago.

Figure 7:
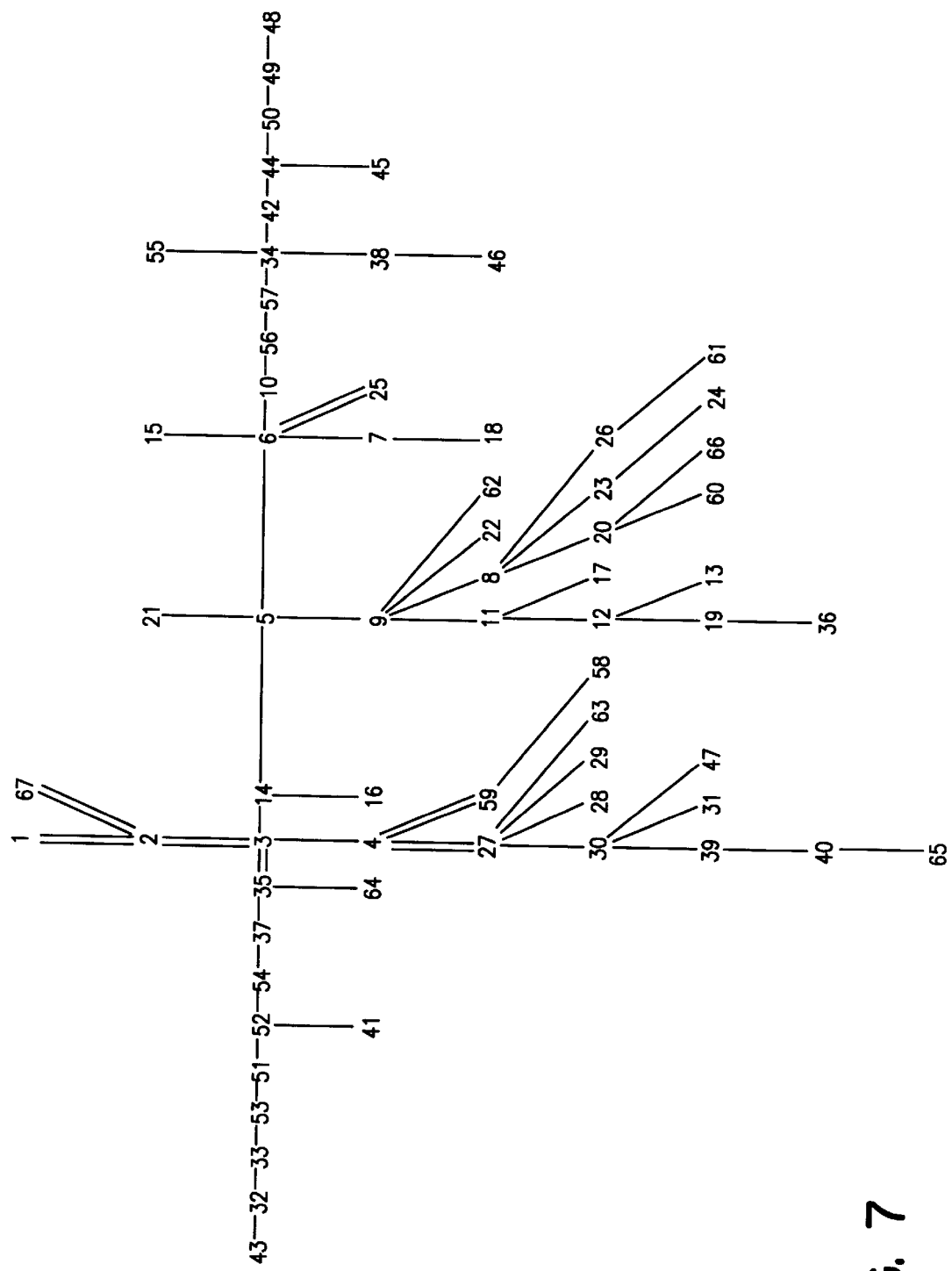
FIG. 7 is a schematic representation of the Graziosi genealogical tree. The numbers refer to the haplotype reported in Table III. The single lines connect haplotypes differing for one locus; double lines connect haplotypes differing for two loci.

Apparently this surname is of polyphyletic origin but a more general view can be obtained from the dendrogram reported in FIG. 7. Most of the dendrogram is justified by single mutations (single lines connecting each haplotype in FIG. 7) however, 7 double mutations (double lines) have also occurred. The double mutation divide the tree into three main sectors at the level of haplotypes 3 and 4.

The branch at the left of haplotype 3 comprises people living in Central Italy (L'Aquila) as well as North-West Italy (Milano), France and Canada.

The second branch, from haplotype 27 downwards, shows a core of people centered around Rimini, some representative in Rome and scattered people in the North-East Italy. The origins of the 12 identical people of haplotype 39 were studied in more detail. Utilizing a registry maintained in a church of a village close to Rimini, it has been possible to demonstrate their common origin from an ancestor who lived between 1700 and 1800.

The third branch, on the right of haplotype 3, shows the largest variability and contains a variety of different groups. The majority of people in this group are distributed in Central Italy with important branches in Avellino and the USA. In particular the origin of some members of this group was investigated with the following results:

1) In all the cases of identity of haplotype it was possible to demonstrate kinship.
2) The Australian AU1 is relative to TN1 and both have familial origin in Central Italy
3) The Argentine AR1 is father to AR2 and U4 and they are the 3rd and 4th generation of a Graziosi who emigrated from Central Italy, although they do not know their exact place of origin.
4) Many members of the Graziosi community presently living in Long Island (USA) declare a long standing as well as recent immigration from Avellino, in accordance with their haplotype.
5) UK1 is father to UK2 and their origin has been traced back through many centuries to the village of Subbiaco, between Roma and L'Aquila.
6) The Dutch NL1 and 2 are relatives and their family originates from Roma.

The ancient origin of the Graziosi surname is evidenced by an inscription dated 1537 which has been found in the castle of Subbico. Thus the Graziosis had at least 5 centuries both for emigrating as well as for accumulating mutations on the Y chromosome. All these historical and genealogical data are in accordance with the Genealogical Tree of FIG. 7.

The Geneaological Tree of Different Families

Table VI sets forth a list of all the haplotypes identified in individual blood or fingernail samples isolated from Trieste and Friuli.

TABLE IV

| N. | Haplotype | N. | Haplotype | N. | Haplotype | N. | Haplotype |
|---|---|---|---|---|---|---|---|
| 1 | 21,251,212 | 30 | 32,254,332 | 59 | 52,384,312 | 88 | 23,361,213 |
| 2 | 21,253,222 | 31 | 32,261,213 | 60 | 11,362,212 | 89 | 25,342,211 |
| 3 | 21,262,312 | 32 | 32,281,212 | 61 | 11,363,212 | 90 | 31,232,532 |
| 4 | 21,351,322 | 33 | 32,381,214 | 62 | 11,372,212 | 91 | 31,252,332 |
| 5 | 21,353,223 | 34 | 32,383,312 | 63 | 12,372,212 | 92 | 31,343,332 |
| 6 | 21,354,222 | 35 | 32,554,322 | 64 | 21,133,322 | 93 | 31,344,333 |
| 7 | 21,361,220 | 36 | 33,152,212 | 65 | 21,243,321 | 94 | 31,352,214 |
| 8 | 21,363,311 | 37 | 33,361,212 | 66 | 21,243,421 | 95 | 31,353,222 |
| 9 | 21,365,322 | 38 | 34,353,221 | 67 | 21,342,222 | 96 | 31,354,232 |
| 10 | 21,384,312 | 39 | 34,383,211 | 68 | 21,342,322 | 97 | 31,364,412 |
| 11 | 21,463,322 | 40 | 41,353,212 | 69 | 21,342,323 | 98 | 31,373,211 |
| 12 | 21,474,321 | 41 | 41,355,312 | 70 | 21,343,221 | 99 | 31,443,212 |
| 13 | 21,474,322 | 42 | 41,355,314 | 71 | 21,344,331 | 100 | 31,452,222 |
| 14 | 22,243,311 | 43 | 41,355,322 | 72 | 21,352,322 | 101 | 31,453,212 |
| 15 | 22,251,212 | 44 | 41,364,212 | 73 | 21,352,332 | 102 | 31,474,312 |
| 16 | 22,364,312 | 45 | 41,365,212 | 74 | 21,353,213 | 103 | 32,451,213 |
| 17 | 22,472,211 | 46 | 41,365,312 | 75 | 21,353,321 | 104 | 32,452,214 |
| 18 | 23,252,212 | 47 | 41,375,212 | 76 | 21,353,322 | 105 | 32,481,213 |
| 19 | 23,252,214 | 48 | 41,384,212 | 77 | 21,354,331 | 106 | 34,243,221 |
| 20 | 23,362,322 | 49 | 41,385,312 | 78 | 21,360,213 | 107 | 41,354,212 |
| 21 | 24,351,211 | 50 | 41,475,312 | 79 | 21,363.,23 | 108 | 41,463,212 |
| 22 | 24,353,311 | 51 | 42,254,312 | 80 | 21,451,323 | 109 | 51,354,212 |
| 23 | 31,352,213 | 52 | 42,363,212 | 81 | 21,452,222 | 110 | 21,352,222 |
| 24 | 31,355,212 | 53 | 42,373,312 | 82 | 21,452,323 | 111 | 21,354,321 |
| 25 | 31,355,312 | 54 | 42,374,312 | 83 | 21,453,322 | 112 | 24,352,311 |
| 26 | 31,363,312 | 55 | 42,473,312 | 84 | 22,231,211 | | |
| 27 | 31,364,332 | 56 | 42,564,312 | 85 | 22,242,212 | | |
| 28 | 31,365,312 | 57 | 45,253,211 | 86 | 22,242,222 | | |
| 29 | 31,365,322 | 58 | 51,385,212 | 87 | 23,241,222 | | |

Figure 8:
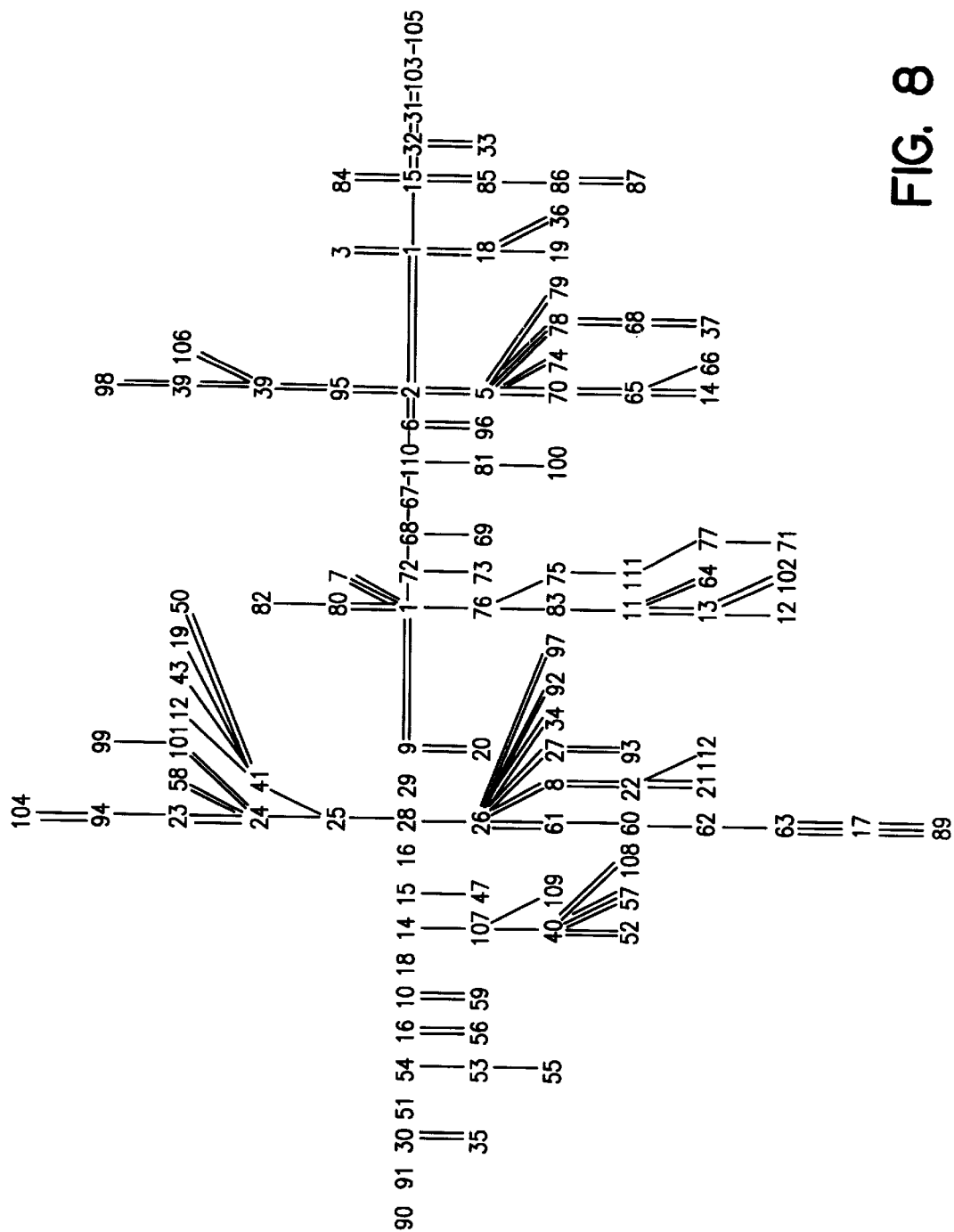
FIG. 8 is a schematic representation of a "tree" of genealogical trees generated by comparing the haplotypes identified in Trieste and Friuli.

The same technique described in the above example for assessing degree of relatedness between individuals with the same surname can also be used for constructing a Genealogical Tree of different families. The possible combinations are rather high. An example is illustrated in FIG. 8. The figure depicts a dendrogram of all the different haplotypes (112) of the population study of Trieste and Friuli (Table IV). The dendrogram is justified by a total of 180 mutations with 111 connections. About 44% of the connections involve only one mutation. Notably the majority of the Trieste samples are clustered on the left hand side of the dendrogram thus demonstrating the ability of the method for discriminating two neighbouring small populations.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for determining the degree of relatedness between two or more individuals having the same or a different surname, comprising:
   a) obtaining a DNA sample from said individuals;
   b) amplifying said DNA by polymerase chain reaction using primers specific for Y chromosome polymorphisms at predetermined loci, said loci being selected from the group consisting of DYS19, DYS388, DYS389A, DYS389B, DYS390, DYS391, DYS392, DYS393, AND YCA2;
   c) determining the haplotypes of said individuals; and
   d) comparing said haplotypes across a plurality of predetermined loci to determine the degree of relatedness between said individuals.

2. The method as claimed in claim 1, wherein said DNA sample is isolated from a source selected from the group consisting of blood cells, fingernail slices and hair follicles.

\* \* \* \* \*